United States Patent [19]

Wettling et al.

[11] Patent Number: 5,614,646

[45] Date of Patent: Mar. 25, 1997

[54] SELECTIVE HYDROGENATION OF AROMATIC GROUPS IN THE PRESENCE OF EPOXY GROUPS

[75] Inventors: Thomas Wettling; Ludwig Schuster, both of Limburgerhof; Jochem Henkelmann, Mannheim, all of Germany

[73] Assignee: BASF Aktiengesellschaft, Ludwigshafen, Germany

[21] Appl. No.: 579,728

[22] Filed: Nov. 17, 1995

Related U.S. Application Data

[63] Continuation of Ser. No. 422,926, Apr. 17, 1995, abandoned.

[30] Foreign Application Priority Data

Apr. 22, 1994 [DE] Germany ............................. 44 14 089.4

[51] Int. Cl.$^6$ ........................ C07D 301/00; C07D 303/27
[52] U.S. Cl. ............................. 549/540; 549/560
[58] Field of Search ................................. 549/540

[56] References Cited

U.S. PATENT DOCUMENTS

| 2,809,177 | 10/1957 | Shukal | 549/540 |
| 2,822,368 | 2/1958 | Rowland et al. | 549/540 |
| 3,336,241 | 8/1967 | Shokal | |
| 3,966,636 | 6/1976 | Jenkins | |
| 4,847,394 | 7/1989 | Schuster | 549/540 |
| 5,391,773 | 2/1995 | Puckette | 549/540 |
| 5,406,007 | 4/1995 | Falling | 549/540 |
| 5,530,147 | 6/1996 | Wettling et al. | 549/540 |

FOREIGN PATENT DOCUMENTS

| 545154 | 6/1993 | European Pat. Off. |
| 3629632 | 3/1988 | Germany |
| 3919228 | 12/1990 | Germany |
| 402743 | 11/1933 | United Kingdom |

*Primary Examiner*—Joseph E. Evans
*Attorney, Agent, or Firm*—Keil & Weinkauf

[57] ABSTRACT

A process for the selective hydrogenation of aromatic groups of organic molecules carrying at least one aromatic group and one epoxy group with hydrogen in the presence of a ruthenium-containing catalyst, in which the hydrogenation is carried out in the presence of from 0.2 to 10 wt % of water, based on the reaction mixture.

3 Claims, No Drawings

SELECTIVE HYDROGENATION OF AROMATIC GROUPS IN THE PRESENCE OF EPOXY GROUPS

This application is a continuation of application Ser. No. 08/422,926, filed on Apr. 17, 1995, now abandoned.

The present invention relates to an improved process for the selective hydrogenation of aromatic groups of organic molecules carrying at least one aromatic group and one epoxy group with hydrogen in the presence of a ruthenium-containing catalyst.

U.S. Pat. No. 3,336,241 teaches the hydrogenation of aromatic epoxy compounds using rhodium and ruthenium catalysts. The activity of the catalysts decreases after one hydrogenation to such an extent that, in an industrial process, the catalyst must be changed after each hydrogenation. U.S. Pat. No. 3,966,636 teaches a process for the regeneration of rhodium and ruthenium catalysts that have become deactivated during the hydrogenation of 2,2-di-[p-glycidoxiphenyl]propane The problem to be solved was to provide a selective hydrogenation process in which the catalysts employed can be used for hydrogenations without purification a number of times.

DE-A 3,629,632 and DE-A 3,919,228 teach the selective hydrogenation of di[glycidoxiphenyl]methane and 2,2-di-[p-glycidoxiphenyl]propane respectively over ruthenium oxide hydrate. According to this teaching it is again recommendable to regenerate the catalysts after each hydrogenation. This involves problems arising in the separation of the finely divided catalyst, which can in most cases only be dissolved by using filtering auxiliaries. However, in order to work up the catalysts, these must be separated from the filtering auxiliaries Another object of the present invention was therefore to provide a process that allows for easy removal of the catalyst ruthenium oxide hydrate from the hydrogenated effluent.

Acccordingly, we have found the process defined above, wherein the hydrogenation is carried out in the presence of from 0.2 to 10 wt. % of water, based on the reaction mixture.

Suitable starting compounds are all such organic molecules which carry at least one aromatic group and one epoxy group. The compounds concerned may be monomeric, oligomeric or polymeric compounds. Examples of suitable starting compounds for the process of the invention are the following individual substances and classes of substances:

Products of the reaction of bisphenol A or bisphenol F with epichlorohydrin

Bisphenol A or bisphenol F and epichlorohydrin can be caused to react with bases in known manner (eg, *Ullmanns Encyclopedia of Industrial Chemistry*, 5th Ed., VCH (1987) Vol. A9, p. 547) to produce glycidyl ethers of the general formula I:

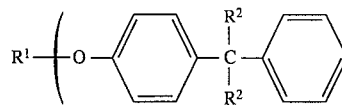
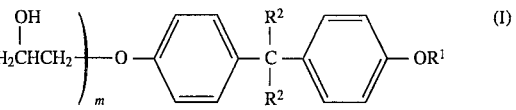

in which

R¹ stands for

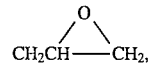

R² stands for hydrogen or a methyl group and m stands for zero to 40

Phenol- and cresol-epoxy novolaks

Novolaks of the general formula II are obtainable by the acid-catalyzed reaction of phenol and cresol respectively and epoxidization of the products of the reaction (cf, eg, bis[4-(2,3-epoxypropoxy)phenyl]methane):

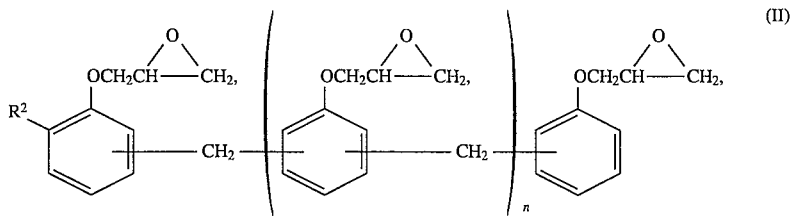

in which R² stands for hydrogen or a methyl group and n for 0 to 40

Glycidyl ethers of products of the reaction of phenol with an aldehyde

Glycidyl ethers are available by the acid-catalyzed reaction of phenol with aldehydes followed by epoxidization with epichlorohydrin, eg, 1,1,2,2-tetrakis-[4-(2,3-epoxypropoxy)phenyl]ethane is available from phenol and glyoxal.

Aromatic glycidylamines

Examples thereof are as follows: the triglycidyl compound of p-aminophenol, 1-(2,3-epoxypropoxy)-4-[N,N-bis(2,3-epoxypropyl)amino]benzene, and the tetraglycidyl compound of methylenediamine bis{4-[N,N-bis(2,3-epoxypropyl)amino]phenyl}methane Other specific examples are:

1,1,2,2-tetrakis[4-(2,3-epoxypropoxy)phenyl]ethane, isomers of tris[4-(2,3-epoxypropoxy)phenyl]methane, 2,5-bis [(2,3-epoxypropoxy)phenyl]octahydro-4,7-methano-5H-indene.

Preferred starting compounds are di[p-glycidoxiphenyl] methane and 2,2-di-[p-glycidoxiphenyl]-propane and oligomers of these compounds.

Suitable catalysts for the process of the invention are homogeneous and heterogeneous ruthenium catalysts. Metallic ruthenium on a support consisting of carbon or aluminum oxide is as suitable as ruthenium vapor-deposited onto metal surfaces. Such catalysts are commercially available or are obtainable by methods known per se. However, ruthenium oxide hydrate is preferred, which can be used as homogeneous material or as active material attached to a heterogeneous support. This ruthenium compound, which has the formula $Ru_2O_3 \cdot xH_2O$ where x can assume a value above 1, is obtained as a water-moist precipitate by the reaction of an aqueous solution of ruthenium(III) chloride hydrate $RuCl_3 \cdot 3H_2O$ with caustic soda solution followed by washing with water for the removal of the chloride ions. The amount of the catalyst is usually in the region of from 0.01 to 1 wt. % of ruthenium, based on the starting compound to be hydrogenated.

Since the hydrogenations of the invention are carried out in many cases with viscous products it may be advantageous to effect the reaction in a solvent. Preferred solvents are ethers, eg, tetrahydrofuran, dioxan, tert-butylmethyl ether, glycol dimethyl ether and methoxypropanol. The amount of the solvent is generally from 5 to 80 Uwt %, based on the reaction mixture.

Furthermore, there are added to the reaction mixture from 0.2 to 10 wt % of water, based on the reaction mixture. Whilst the use of smaller amounts has no discernable effect, the use of distinctly greater amounts causes undesirable hydrolyric opening of the epoxide ring to a considerable extent.

The hydrogenation is effected unter pressure which is usually in the region of from 100 to 320 bar. The temperature of reaction is usually from 30° to 80° C., preferably from 40° to 70° C.

The reaction can be effected batchwise or continuously. To this end the starting compounds, the catalyst, water and optionally solvents can be intermixed and caused to react with hydrogen in a reactor. The reaction is generally complete after from 2 to 10 hours. The reaction mixture can then be depressurized to standard pressure, separated from catalyst, for example by filtration, and freed from all of the volatile constituents by distillation. The separated catalyst can be recycled, if desired after replenishment with fresh catalyst, to the hydrogenation process.

The process of the invention has the advantage that following a hydrogenation the catalyst is still sufficiently active to be capable of being used for further hydrogenations. It has been found to be advantageous to replace a small portion, say, a quarter, of the used catalyst, after each hydrogenation and prior to recycling, by fresh catalyst, by which means the process engineering costs incurred for catalyst regeneration are considerably reduced.

Furthermore, when ruthenium oxide hydrate is used, the present invention allows the catalyst to be separated from the product in a simple manner.

The end products are useful as lightproof coating compositions, casting resins and laminates.

EXAMPLES

Examples 1 to 4

In an autoclave, 1000 g of a bisglycidyl ether of a phenol/formaldehyde condensate (bis[4-(2,3-epoxypropoxy)phenyl]methane having an epoxide equivalent weight of 168), 40 g of a ruthenium oxide hydrate suspension in tetrahydrofuran (THF) having a content of 1 g of ruthenium (obtained by reacting $RuCl_3 \cdot 3H_2O$ with caustic soda solution at pH 8 and washing the resulting precipitate with water and THF), water and 960 g of THF were hydrogenated at 50° C. and a pressure of 250 bar, with hydrogen. The amount of water in the batch and the reaction time are indicated in Table 1 below. The hydrogenated effluents were filtered and were colorless. Following the removal, by distillation, of volatile constituents there were isolated from 1010 to 1030 g of product.

TABLE 1

| Ex. | Water Content [wt %] | Reaction Time [h] | Aromatics Content in Product | Epoxide Equivalent Weight |
|---|---|---|---|---|
| 1 | 1.0 | 6.0 | 4% | 188 |
| 2 | 2.5 | 4.0 | Trace | 191 |
| 3 | 5.3 | 3.0 | 0 | 197 |
| 4 | 7.5 | 2.5 | 0 | 213 |

The epoxide equivalent weight was determined according to ASTM D 1652-88 and gives the mean molecular weight of the end product divided by the mean number of epoxy groups per molecule. This value is thus a measure of the selectivity of the hydrogenation reaction.

Example 5 (for Comparison)

This was carried out as in Examples 1 to 4 but without the addition of water

Following a reaction time of 8 h there were isolated 1010 g of product having an aromatics content of 3% and an epoxide equivalent weight of 177.

The effluent was dark colored after filtration and could only be decolored by the addition of activated charcoal.

The process of the invention makes it possible to produce products of greater purity over shorter reaction times. Furthermore, complete separation of the catalyst from the product involves less process engineering than in the comparative test.

Example 6

In an autoclave, 1000 g of the poly(glycidyl ether) described in Example 1, 40 g of ruthenium oxide hydrate/THF suspension having a ruthenium content of 1 g, 40 g of water, and 920 g of THF were hydrogenated under a pressure of 250 bar for 4 h at from 50° to 70° C., with hydrogen. Following depressurization to standard pressure, the catalyst was allowed to settle over 12 h. 1400 g of the supernatant solution were withdrawn via a vertical tube. The reaction mixture was topped up with the bisglycidyl ether, water, THF, and catalyst to 2000 g whilst, however, instead of 1 g of ruthenium only 0.25 g were added (ratio by weight of poly(glycidyl ether) to THF 10:9, water content 2.6wt %). In three subsequent hydrogenations 2020 g of effluent were withdrawn in each case and replaced as described. All of the reaction products were colorless after filtration, virtually free from aromatics and possessed epoxide equivalent weights of from 180 to 185.

By adding only small amounts of fresh catalyst after each hydrogenation it is possible to carry out several hydrogenations at constant product quality.

Example 7 (for Comparison, Without the Use of Water)

1000 g of the bisglycidyl ether characterized in Example 1, 40 g of the ruthenium oxide hydrate/THF suspension having a content of ruthenium of 1 g, and 900 g of THF were hydrogenated for 4 h at from 50° to 70° C. and 250 bar, with hydrogen. The catalyst was allowed to settle over 12h, and 1400 g of the supernatant solution were withdrawn as described in Example 6 via a vertical tube. The entrained catalyst was removed by centrifugation—complete separation not being achieved—and the catalyst thus isolated was recycled to the reactor together with the aforementioned amounts of poly(glycidyl ether) and THF. Renewed hydrogenation came to a halt after only low hydrogen take-up.

The catalyst was deactivated after one hydrogenation.

Example 8 (Continuous Procedure)

A bisglycidyl ether, such as characterized in Example 1, was continuously hydrogenated in tetrahydrofuran in a ratio by weight of 1:0.96 in the presence of 0.1 wt % of ruthenium, based on the reaction mixture, which was used in the form of the ruthenium oxide hydrate suspension described in Example 1, and 0.5 wt % of water, based on the reaction mixture, at from 50° to 70° C. and a hydrogen pressure of 250 bar for a mean residence time of 10 h. The effluent was separated from the catalyst and the volatile components were removed by distillation. The remaining product was colorless (aromatics content from 6.7 to 9.4%, epoxide equivalent value from 179 to 187). The separated catalyst was enriched with 0.03wt. %, based on the reaction mixture, of fresh ruthenium (in the form of ruthenium oxide hydrate suspension) and recycled to the reaction with the starting compounds.

We claim:

1. In a process for the selective hydrogenation with hydrogen of aromatic groups of organic molecules carrying at least one aromatic group and one epoxy group, the improvement which comprises: adding to the reaction mixture from 0.2 to 10 wt % of water, based on the reaction mixture and carrying out the hydrogenation in the presence of ruthenium oxide hydrate as a catalyst.

2. A process as defined in claim 1, wherein di[p-glycidoxiphenyl]methane or 2,2-di-[p-glycidoxiphenyl]propane is hydrogenated.

3. A process as defined in claim 1, wherein the hydrogenation is carried out at from 40° to 70° C.

* * * * *